(12) United States Patent
Laske et al.

(10) Patent No.: US 7,162,309 B2
(45) Date of Patent: Jan. 9, 2007

(54) EPICARDIAL LEAD DELIVERY SYSTEM AND METHOD

(75) Inventors: Timothy G. Laske, Shoreview, MN (US); James F. Kelley, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 558 days.

(21) Appl. No.: 10/408,426

(22) Filed: Apr. 7, 2003

(65) Prior Publication Data

US 2004/0199236 A1 Oct. 7, 2004

(51) Int. Cl.
*A61N 1/05* (2006.01)
*A61B 5/042* (2006.01)

(52) U.S. Cl. ..................... 607/122; 600/386

(58) Field of Classification Search ............... 607/119, 607/122, 124, 126–128; 606/129; 600/386
See application file for complete search history.

(56) References Cited

U.S. PATENT DOCUMENTS

| | | | |
|---|---|---|---|
| 3,680,544 A | 8/1972 | Shinnick et al. | |
| 5,033,477 A | 7/1991 | Chin et al. | |
| 5,117,828 A * | 6/1992 | Metzger et al. | 600/380 |
| 5,309,896 A | 5/1994 | Moll et al. | |
| 5,336,252 A | 8/1994 | Cohen | |
| 5,397,341 A * | 3/1995 | Hirschberg et al. | 607/122 |
| 5,402,772 A | 4/1995 | Moll et al. | |
| 5,465,711 A | 11/1995 | Moll et al. | |
| 5,575,759 A | 11/1996 | Moll et al. | |
| 5,826,576 A * | 10/1998 | West | 600/373 |
| 5,865,728 A | 2/1999 | Moll et al. | |
| 5,893,296 A | 4/1999 | Rosheim | |
| 5,967,977 A * | 10/1999 | Mullis et al. | 600/380 |
| 5,979,264 A | 11/1999 | Rosheim | |
| 6,010,526 A | 1/2000 | Sandstrom et al. | |
| 6,105,455 A | 8/2000 | Rosheim | |
| 6,418,811 B1 | 7/2002 | Rosheim | |

* cited by examiner

*Primary Examiner*—Robert E. Pezzuto
*Assistant Examiner*—Terri Lynn Smith
(74) *Attorney, Agent, or Firm*—Michael C. Soldner; Carol F. Barry; Girma Wolde-Michael

(57) ABSTRACT

A manipulator joined to a distal end of a delivery system shaft includes a plurality of arms and a collar. A proximal portion of each of the arms is joined to the shaft and a distal portion of each of the arms is joined to the collar such that the collar is substantially aligned with a lumen of the shaft. The lumen and the collar slideably and rotatably engage a medical electrical lead while a plurality of control wires, adapted to manipulate the manipulator, join to each of the plurality of manipulator arms in proximity to the distal end of the shaft.

12 Claims, 12 Drawing Sheets

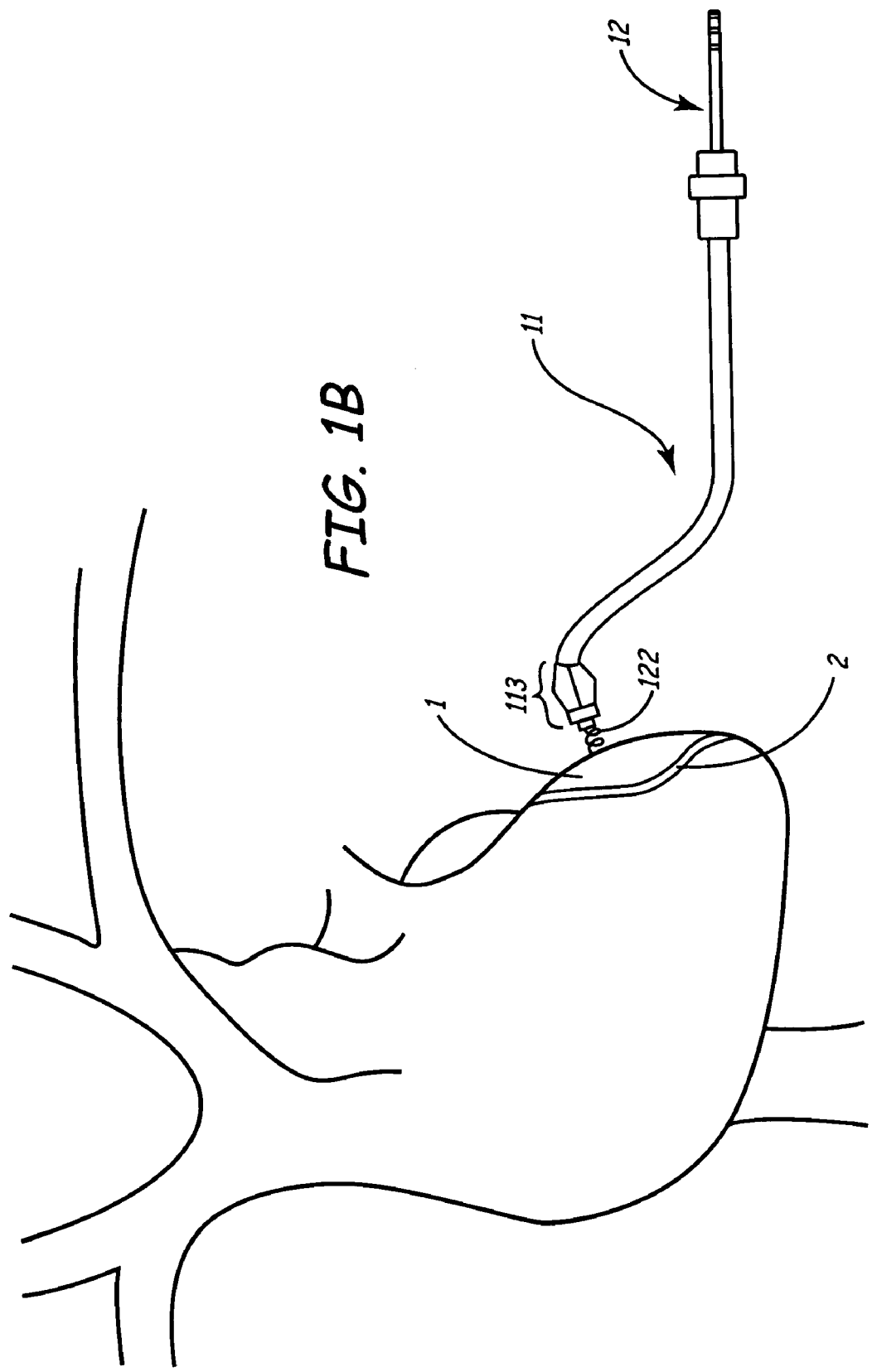

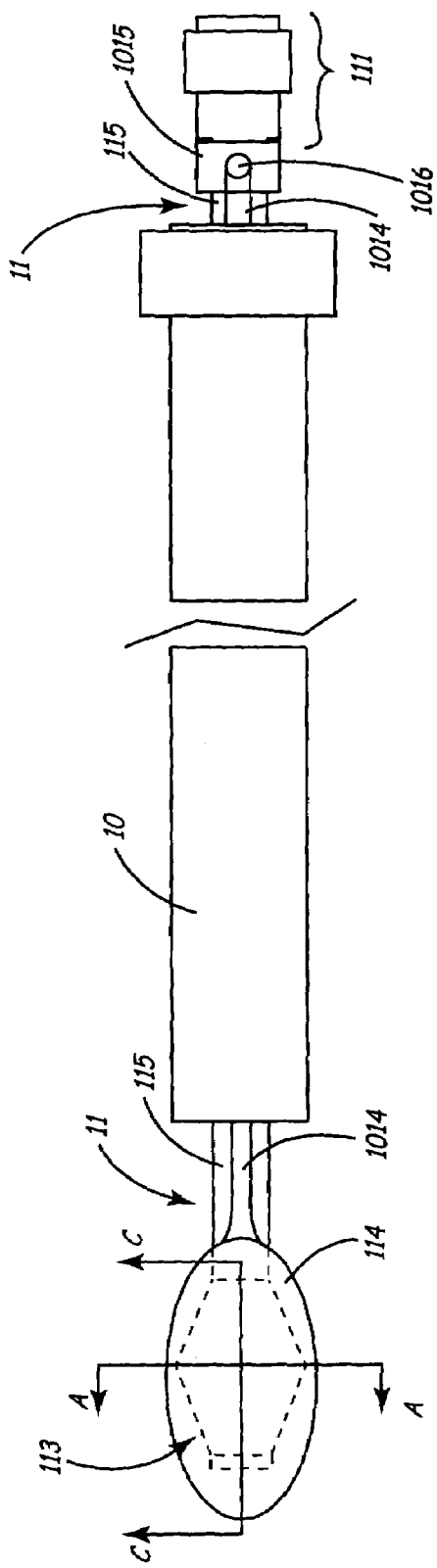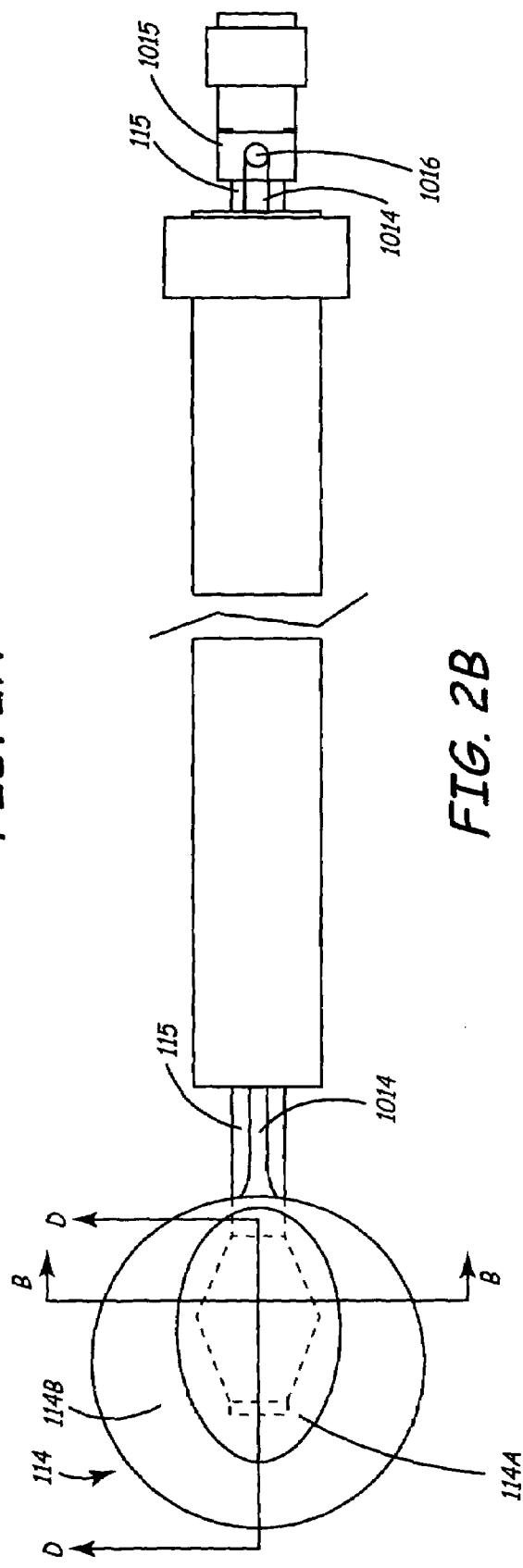
FIG. 2A
FIG. 2B

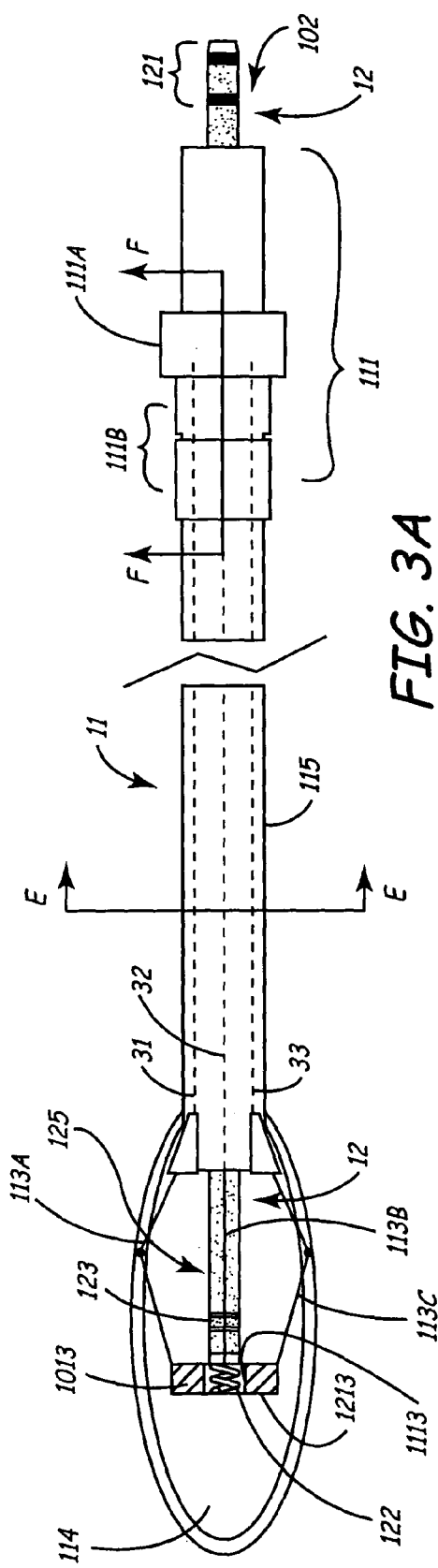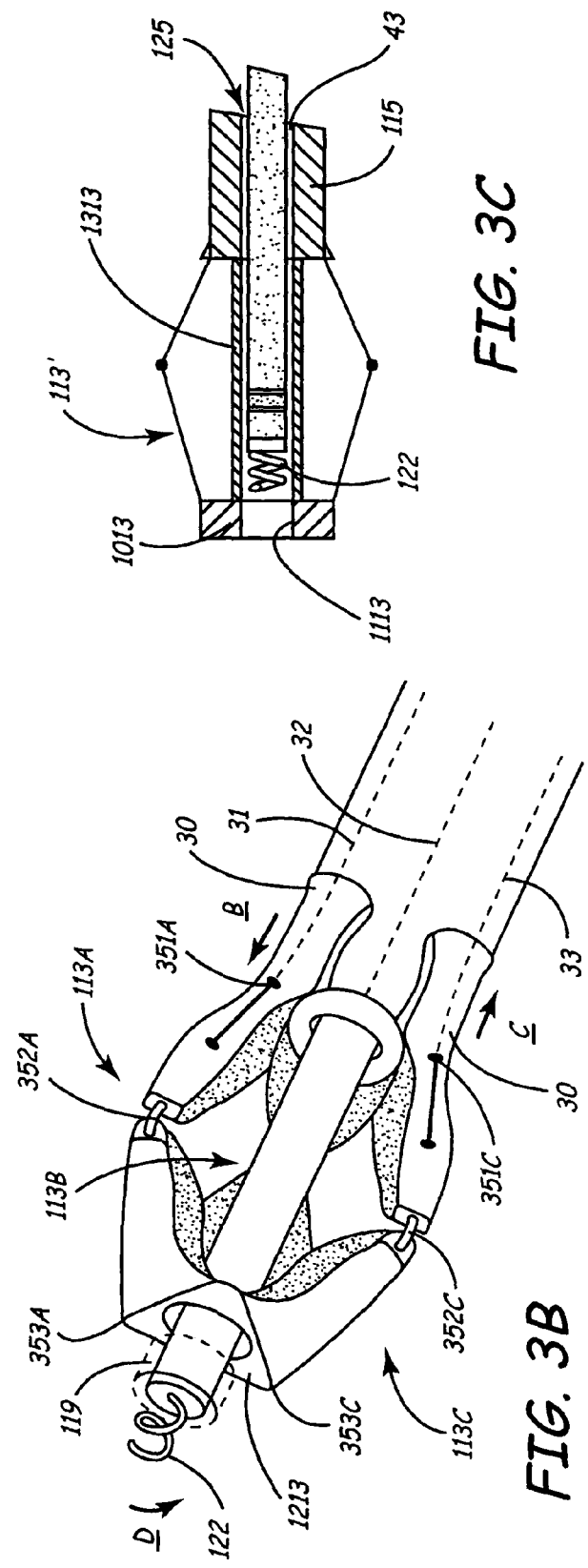

US 7,162,309 B2

EPICARDIAL LEAD DELIVERY SYSTEM AND METHOD

FIELD OF THE INVENTION

Embodiments of the present invention relate generally to means for implanting medical electrical leads, and, more specifically to a system and associated method facilitating delivery and fixation of a medical electrical lead on an epicardial surface.

BACKGROUND OF THE INVENTION

Therapeutic electrical stimulation from an implantable medical device may be delivered via pacing and/or defibrillation leads either implanted endocardially, inside the heart, or implanted epicardially, on the outside of the heart. Helical fixation members for screwing into myocardial tissue are employed in endocardial and epicardial pacing and defibrillation leads and the construction of such medical electrical leads are well known in the art. Typically the helical member terminates a distal end of a lead and serves as a stimulating electrode. Alternate embodiments of the present invention relate to a system adapted for delivery of epicardial pacing and/or defibrillation leads. More particularly, embodiments of the present invention, described herein, facilitate a proper orientation of a distal member of a lead, such as a helix, for fixation of the lead to the epicardial surface of the heart.

BRIEF DESCRIPTION OF THE DRAWINGS

FIG. 1B is a schematic of an epicardial surface of a heart wherein a second embodiment of a delivery system according to the present invention is positioned.

FIG. 2A is a plan view of a delivery system catheter, an expandable shroud and a sheath.

FIG. 2B is a plan view of the expandable shroud of FIG. 2A in a deployed state.

FIG. 3A is a plan view with partial section of a lead assembled into the delivery system catheter of FIG. 2A.

FIG. 3B is a perspective view of one embodiment of a delivery catheter manipulator.

FIG. 3C is a cross-section of plan view of an alternate embodiment of a delivery catheter manipulator

DETAILED DESCRIPTION OF THE EMBODIMENTS OF THE INVENTION

Figure 1A:
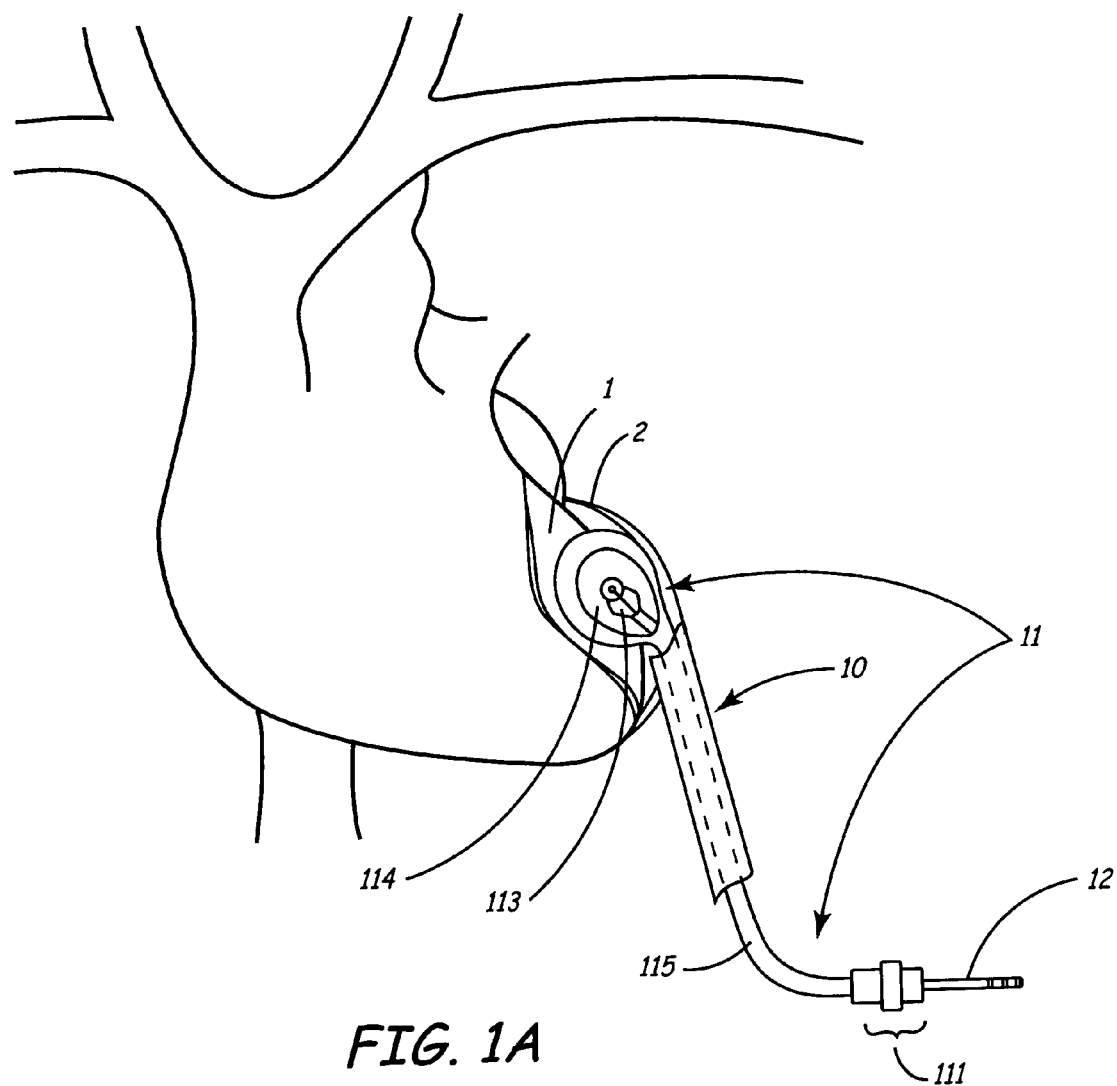
FIG. 1A is a schematic having a partial cut-away view of an epicardial surface of a heart wherein one embodiment of a delivery system according to the present invention is positioned.

FIG. 1A is a schematic having a partial cut-away view of an epicardial surface of a heart wherein one embodiment of a delivery system according to the present invention is positioned. FIG. 1A illustrates a sheath 10 inserted through a pericardial sac 2 surrounding the heart. According to one method, sheath 10 is positioned over a guide wire that has been inserted into the pericardial space, for example from a sub-xyphoid position, techniques associated with such a method are known to those skilled in the art and described in U.S. Pat. Nos. 4,991,571 and 5,336,252. FIG. 1 further illustrates lead delivery catheter 11 including a shaft 115, positioned within sheath 10, and including a manipulator 113 (shown with dashed lines) between an expandable shroud 114 and epicardial surface 1. Although FIG. 1 illustrates lead delivery catheter 11 delivered through sheath 10, delivery catheter 11 may be delivered directly over the aforementioned guide wire without the need for sheath 10. Manipulator 113 is steered via a handle 111, attached near a proximal end of shaft 115, to orient distal end of lead 12 for epicardial fixation, as will be described more fully in conjunction with FIGS. 3–5. Expandable shroud 114 creates a space for movement of manipulator 113 between epicardial surface 1 and pericardial sac 2. In alternate embodiments, expandable shroud 114 is an integral part of sheath 10, an integral part of catheter 11, or a separate assembly and will be further described below, in conjunction with FIGS. 2A–G. A lead 12 is inserted into shaft 115 of catheter 11 either before or after manipulator 113 is oriented. Manipulator 113 is oriented such that a helix electrode 122 (shown in FIG. 1B) terminating a distal end of lead 12 is directed approximately perpendicularly to epicardial surface 1 for fixation.

FIG. 1B is a schematic of an epicardial surface of a heart wherein a second embodiment of a delivery system according to the present invention is positioned. FIG. 1B illustrates lead delivery catheter 11 positioned via a mini-thoracotomy wherein pericardial sac 2 has been excised according to techniques known to those skilled in the art of cardiac surgery. Since epicardial surface 1 is exposed, a shroud, such as expandable shroud 114 described herein, is not necessary. As illustrated in FIG. 1B, manipulator 113 has been oriented so that helix electrode 122 may be screwed into epicardial surface 1.

FIG. 2A is a plan view of catheter 11 within sheath 10. Manipulator 113 is shown with dashed lines, being beneath expandable shroud 114. Shroud 114 is illustrated in a low-profile, or collapsed state, having been passed through sheath 10. FIG. 2B is a plan view of catheter 11 within sheath 10 including expandable shroud 114 in a deployed, or expanded state (as shown in FIG. 1). FIGS. 2A–B illustrate shroud 114 joined to a tube 1014. Tube 1014 extends along a length of shaft 115 to a proximal end 1015 of shaft where tube 1014 joins with an expansion port 1016. Expansion of shroud 114 is controlled via port 1016 and tube 1014. In one embodiment, tube 1014 and port 1016 are an integral part of shaft 115 while, in an alternate embodiment, shroud 114, tube 1014, and port 1016 form a separate assembly. As illustrated in FIG. 2B, shroud 114 includes a core 1 14A and an inflatable border 114B; tube 1014 directs fluid from port 1016 into inflatable border 114B in order to expand shroud 114. In another embodiment shroud is expanded via a spring mechanism activated via port 1016 through tube 1014.

Figure 2C:
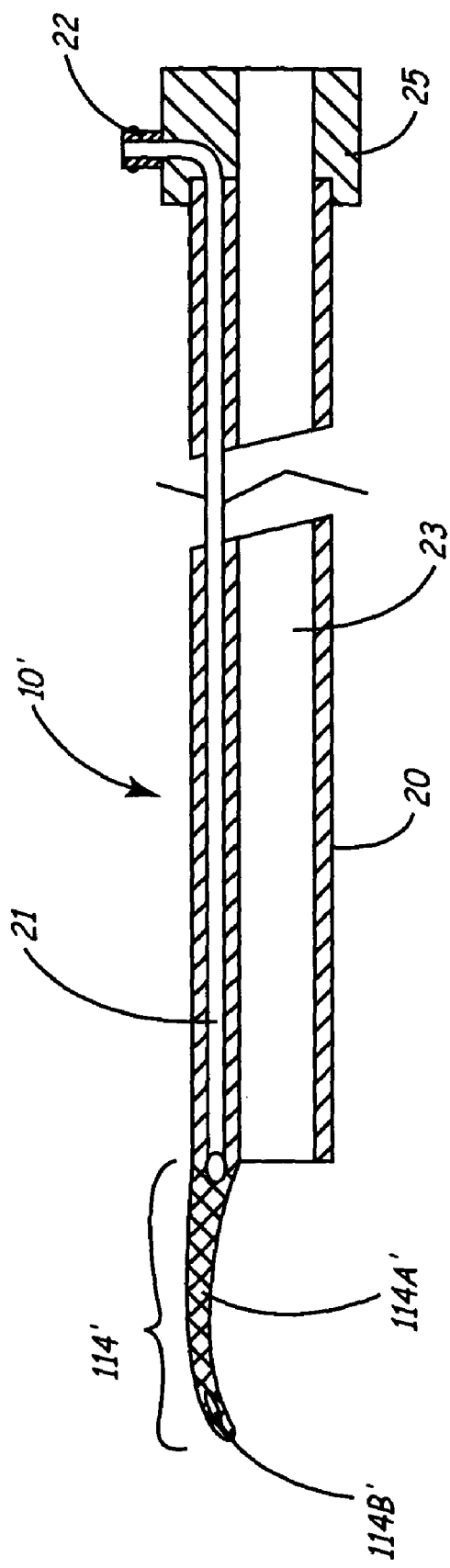
FIG. 2C is an axial cross-section of a sheath including an expandable shroud.

FIG. 2C is an axial cross-section of a sheath 10' including an expandable shroud 114'. As illustrated in FIG. 2C, expandable shroud 114' is an integral part of sheath 10', rather than being an element passed through sheath 10 along with catheter 11, as illustrated in FIGS. 1–2A. FIG. 2C illustrates expandable shroud 114', including a core 114A' and an inflatable border 114B', joined to a sheath shaft 20 including a first lumen 23 to slideably engage a delivery catheter, such as delivery catheter 11, and a second lumen 21 for inflation of border 114B' via a port 22 positioned on a hub 25 terminating a proximal end of sheath 10'.

Figure 2D:
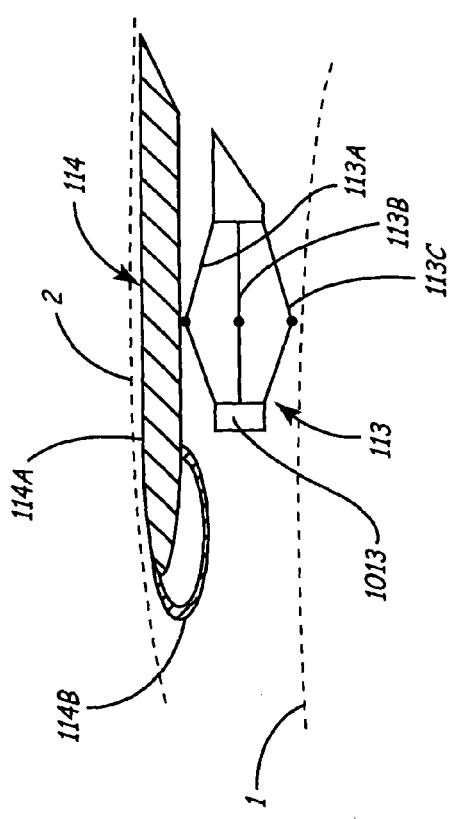
FIGS. 2D–E are section views, through section lines C—C and A—A, respectively, shown in FIG. 2A.
Figure 2E:
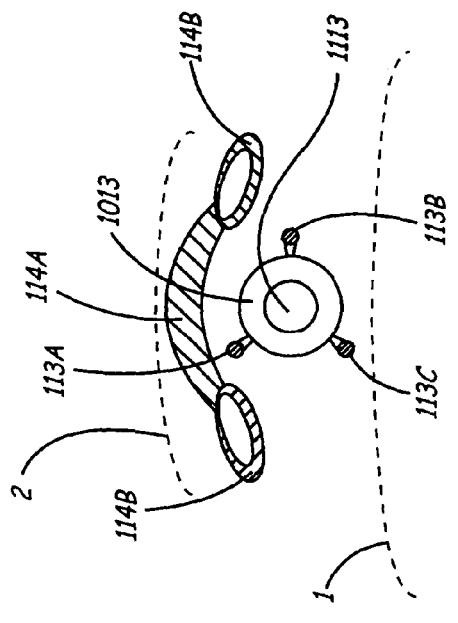
Figure 2F:
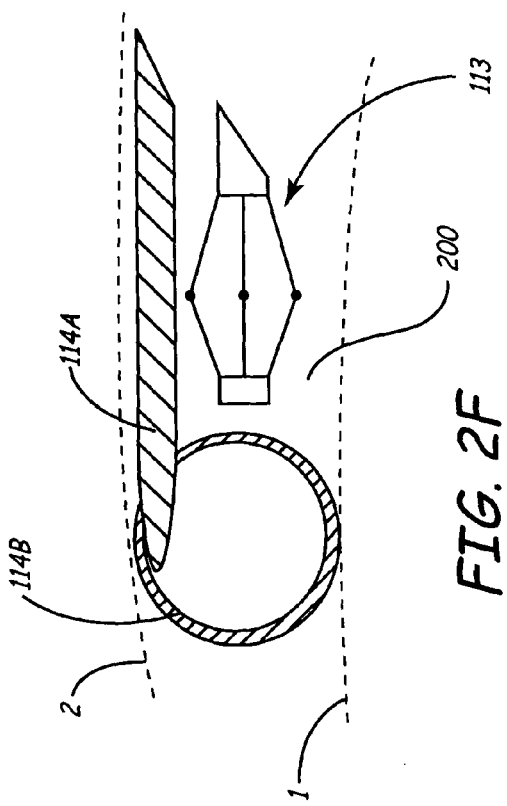
FIGS. 2F–G are section views, through section lines D—D and B—B, respectively, shown in FIG. 2B.
Figure 2G:
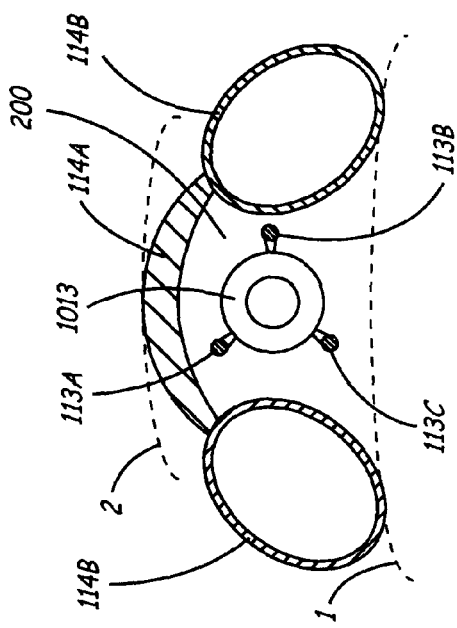

FIGS. 2D–E are section views of catheter 11, through section lines C—C and A—A, respectively, shown in FIG. 2A. FIGS. 2D–E illustrate inflatable border 114B in a deflated stated for passage of shroud 114 and manipulator 113 between epicardial surface 1 and pericardial sac 2. FIGS. 2F–G are section views of catheter 11, through section lines D—D and B—B, respectively, shown in FIG. 2B. FIGS. 2E–F illustrate inflatable border 114B in an inflated state. Once shroud 114 has been positioned between epicardial surface 1 and pericardial sac 2, border 114B is inflated to provide a working space 200 for manipulator 113. In one embodiment, according to the present invention, working space 200 formed by inflation of border 114B is generally cylindrical having a circumference of between approximately 0.5 and approximately 1 inch and a height of between approximately 0.5 and approximately 1 inch.

According to some embodiments, inflatable border 114B is formed from a resilient material, such as a silicone or a cross-linked polyethylene, and joined to core 114A via adhesive or thermal bonding; and core 114A is formed from a biocompatible plastic, relatively rigid or relatively flexible, many alternatives of which are known to those skilled in the art. In an alternate embodiment, according to the present invention, border 114B and core 114A are formed from a single balloon structure, pre-shaped to create a working space, such as working space 200 described above, when inflated. Alternate methods and materials for constructing such balloon-like structures are known to those skilled in the art.

FIGS. 2D–G further illustrate elements of one embodiment of manipulator 113, according to the present invention. Manipulator 113 includes arms 113A, 113B and 113C and a collar 1013 having a lumen 1113 and a distal face 1213 (FIGS. 3A–B). Arms 113A–C create a wrist-like mechanism, to orient collar 1013. Once collar 1013 has been oriented, so that distal face 1213 will be approximately perpendicular to epicardial surface 1 (FIG. 1B), a distal potion 125 of lead 12 (FIGS. 3A–B) is passed through collar 1013 for fixation to surface 1. According to one embodiment of the present invention, manipulator 113 is actuated via handle 111 as is described below in conjunction with FIGS. 3A–B and FIG. 5A–B.

FIG. 3A is a plan view with partial section of lead 12 assembled into catheter 11. Shroud 114 is shown positioned behind manipulator 113 in this view, however, as previously mentioned, shroud 114 is not necessary for other embodiments according to the present invention. FIG. 3A illustrates lead 12 slideably engaged in a lumen 43 (FIG. 3C) of shaft 115 and including a connector 121 terminating a proximal end 102. As further illustrated in FIG. 3A, lead 12 is bipolar, including a ring electrode 123, in proximity to helix 122; in alternate embodiments a lead according to the present invention is unipolar, and in further embodiments a lead includes more than two poles. Although lead 12 is illustrated as a pacing lead, a lead including a defibrillation electrode may also be placed by catheter 11. Details of medical electrical lead construction are known to those skilled in the art.

As illustrated in FIG. 3A distal portion 125 of lead 12 is positioned within manipulator 113 so that helix 122 is temporarily housed within a lumen 1113 of collar 1013 to prevent snagging of helix on peripheral anatomy, as manipulator 113 is being positioned and controlled for proper orientation of collar 1013 at an implant site. Once collar 1013 has been oriented, lead 12 is advanced through delivery catheter 11 so that helix 122 protrudes from collar 1013, as illustrated in FIG. 3B, for contact with implant site on epicardial surface 1 (reference FIG. 1B). In an alternate embodiment distal portion 125 of lead 12 includes an enlarged tip 119 in proximity to helix 122 as illustrated by dashed lines in FIG. 3B. Enlarged tip 119 has a larger diameter than lumen 1113 of collar 1013 so that tension in lead 12 engages tip 119 against distal face 1213 of collar 1013 keeping distal portion 125 and helix 122 in a fixed position within manipulator 113. Helix 122 is fixed into an implant site by rotating lead body 12 at proximal end 102 to screw helix into epicardial surface 1. Helix 122 may function as an electrode and a fixation element or may only serve as a fixation element.

FIG. 3A further illustrates shaft 115 of catheter 11 carrying wires 31, 32, and 33. As illustrated in FIG. 3A, wires 31, 32, and 33 are a means for actuating manipulator 113, being joined to arms 113A, 113B, and 113C, respectively, at one end and joined to a slider 111A of handle 111 at another end. Slider 111A pulls or pushes wires 31, 32, and 33 simultaneously (per Arrow A), while handle 111 pivots about a ball-and-socket pivoting joint 111B to selectively push and pull wires actuating an omni-directional motion of manipulator 113. Handle 111 is presented in cross-section through section line F—F in FIG. 5A and described herein below. An alternate embodiment of a handle is shown in FIG. 5B and will be described herein below. An additional element used to form shaft 115 to facilitate positioning of manipulator 113 is included in alternate embodiments and described in conjunction with FIGS. 6A–B.

FIG. 3B is a perspective view of one embodiment of a delivery catheter manipulator. FIG. 3B illustrates wires 31, 32 and 33 extending out from junctions 30 to join proximal portions of arms 113A, 113B and 113C, respectively, where the wires actuate manipulator 113 by extending or contracting the arms at flexible joints 351A, 352A, and 353A, 351C, 352C, and 353C and, although not labeled in FIG. 3B, at corresponding joints of arm 113B. In one embodiment arms 113A–C are made of a molded plastic such as polypropylene and corresponding flexible joints, such as 351–353A and 351–353B, are formed as 'living hinges'. An arrow B indicates a push from wire 31 and an arrow C indicates a pull from wire 33 resulting in a motion of manipulator in a general direction indicated by arrow D.

FIG. 3C is a cross-section of plan view of an alternate embodiment of a delivery catheter manipulator. FIG. 3C illustrates a manipulator 113' including a guide 1313 positioned between a distal end of catheter shaft 115 and collar 1013 in order to extend lumen 43 for guidance of lead distal end 125. Guide 1313 is adapted to flex with articulations of manipulator 113' and to remain patent for delivery of lead distal end 125 through manipulator 113' after manipulator 113' has steered collar 1013 into an orientation for fixation of helix 122. Guide 1313 is formed, for example, from any flexible biocompatible tubular structure known in the art.

Figure 4B:
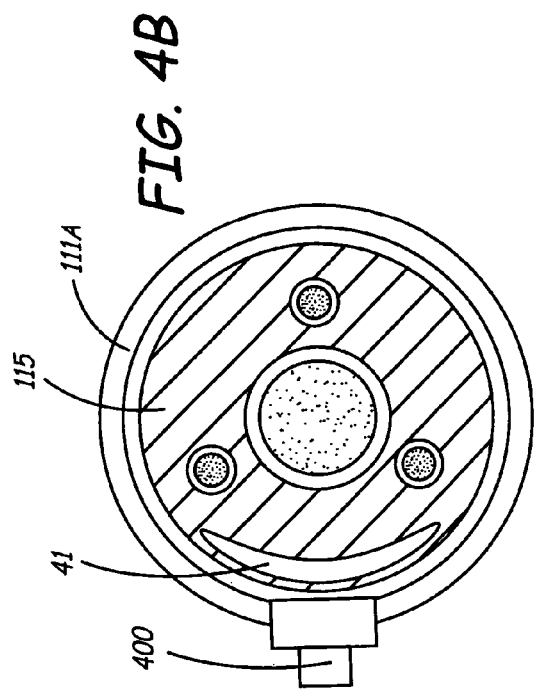
FIGS. 4A–D are cross-section views through section line E—E of FIG. 3A.
Figure 4D:
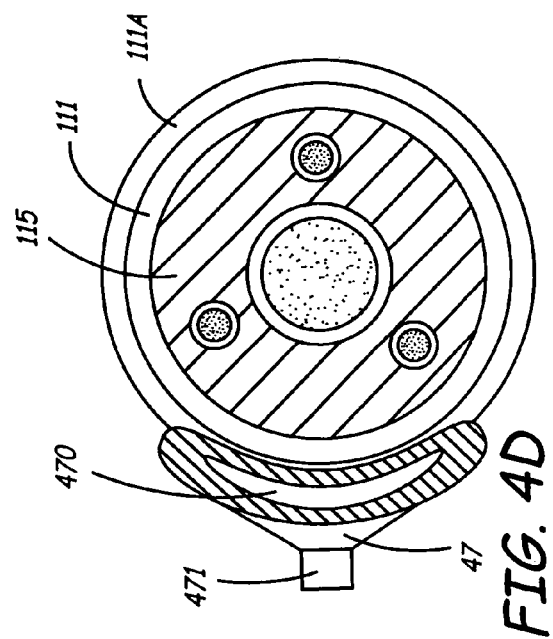
Figure 4A:
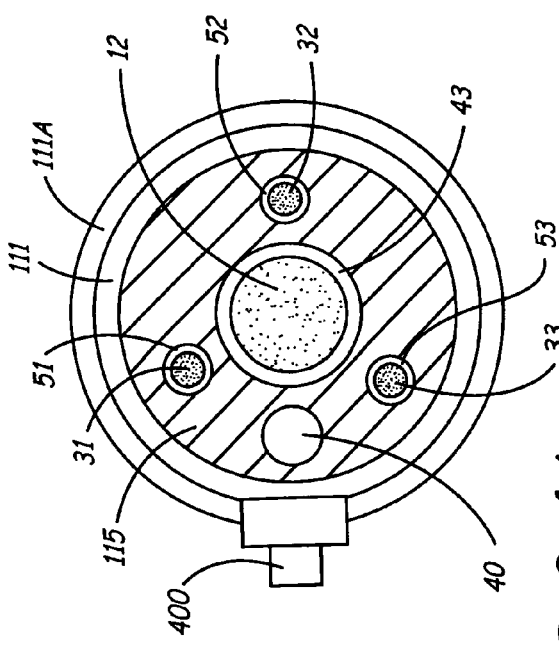

FIGS. 4A–B are cross-section views through section line E—E of FIG. 3A illustrating alternate embodiments of shaft 115 according to the present invention. FIG. 4A illustrates shaft 115 including lumens 51, 52 and 53 slideably engaging wires 31, 32 and 33, respectively, an inflation lumen 40, and lumen 43 engaging lead 12. Wires 31, 32 and 33 extend through lumens 51, 52 and 53 from slider 111A, through pivoting joint 111B, and through shaft 115 to junctions 30 where wires 31, 32 and 33 are mechanically coupled to manipulator arms 113A, 113C and 113B. Inflation lumen 40 extends from an inflation port 400 in proximity to handle 111 (as seen, for example, in FIG. 5A) to shroud 114, where shroud 114 joins to shaft 115, providing a passage for injection of a fluid medium for inflation of shroud 114 as described in conjunction with FIGS. 2A–G. Lumen 43 extends along the entire length of handle 111 and shaft 115 and is shown slideably engaging lead 12. Lumen 43 may also facilitate delivery of catheter 11 over a guide wire as described above in conjunction with FIG. 1A. FIG. 4B illustrates an alternate embodiment of shaft 115 wherein an inflation lumen 41 forms a generally arcuate section.

Figure 4C:
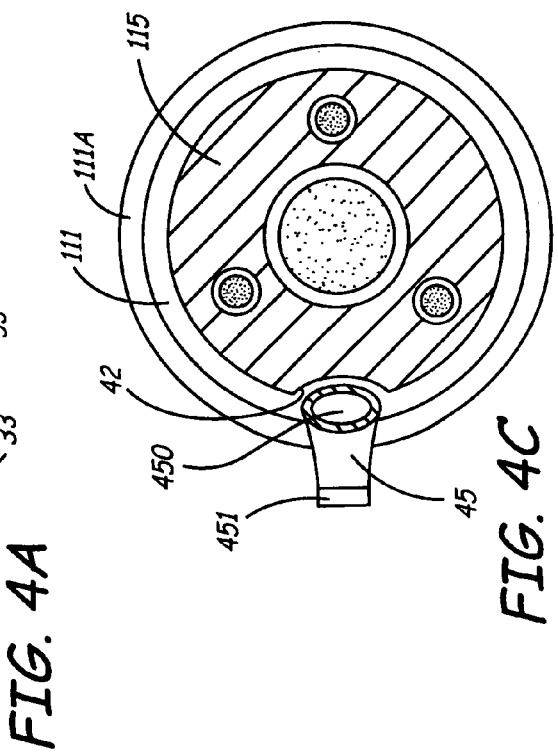

FIGS. 4C–D illustrate alternate embodiments of catheter shaft 115 according to the present invention wherein an inflation lumen is not included in catheter shaft 115. FIG. 4C illustrates a separate elongated shroud shaft 45 including a port 451 and a lumen 450 for inflation of shroud 114. As illustrated in FIG. 4C, one embodiment of catheter shaft 115 includes a groove 42 holding shroud shaft 45 along the length of shaft 115. FIG. 4D illustrates an alternate embodiment of a shroud shaft 47 including a port 471 and an inflation lumen 470 for inflation of shroud 114. Shaft 47 forms a generally arcuate section in order to conform to catheter shaft 115 along the length of shaft 115. In yet another alternate embodiment, a delivery system does not include a shroud at all.

Catheter shaft 115 may be an extruded multi-lumen tubing formed from a polyether block-amide, a polyethylene, a polyester, a polyurethane or any flexible biocompatible material such as is known to those skilled in the art. Shaft 115 may have an outer diameter between approximately 0.1 and approximately 0.5 inch. Lumen 43 may have inner diameter between approximately 0.02 and approximately 0.1 inch; and wire lumens 51–53 may have inner diameters between approximately 0.01 and approximately 0.05 inch. Any one of the lumens may include fluoropolymer liners.

Figure 5A:
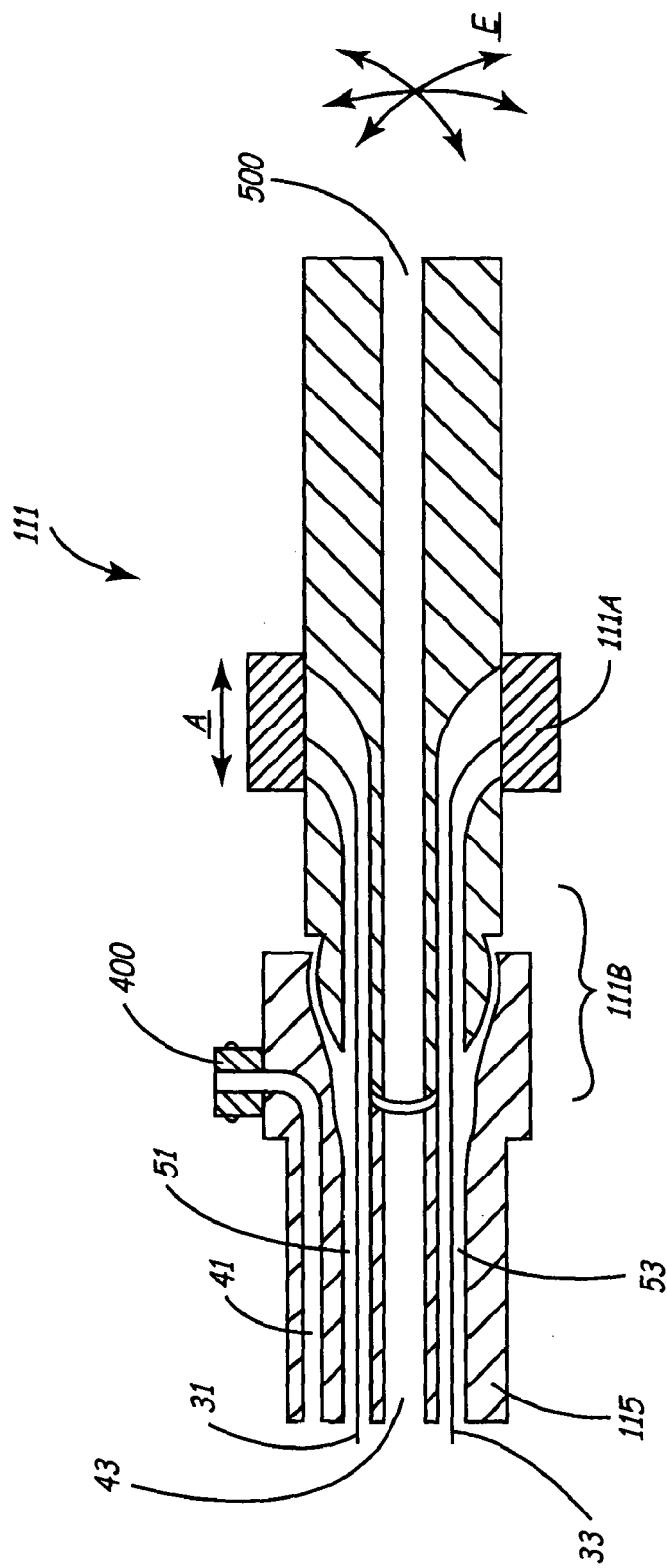
FIG. 5A is a cross-section view through section line F—F of FIG. 3A.
Figure 5B:
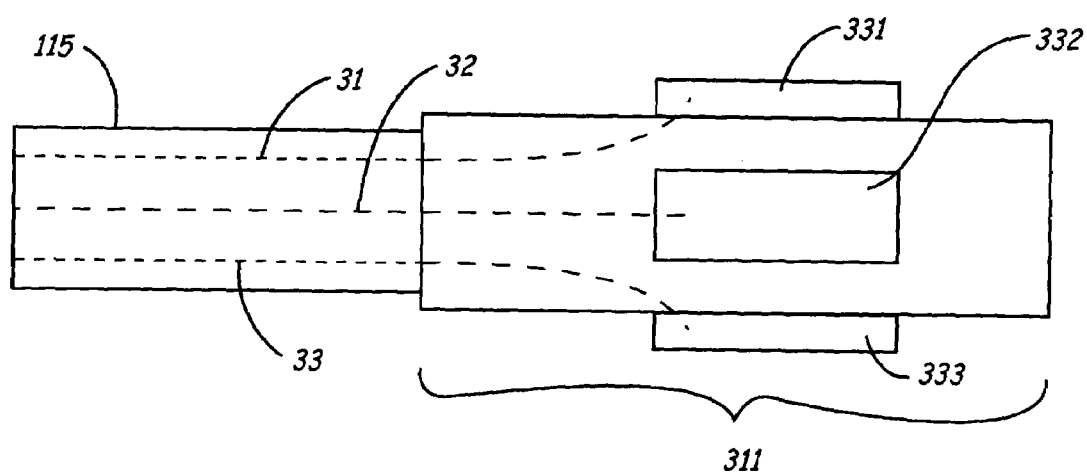
FIG. 5B is a plan view of an alternate embodiment of a handle for a delivery catheter.

FIG. 5A is a cross-section view through section line F—F of FIG. 3A. FIG. 5A illustrates handle 111 terminating a proximal end of shaft 115 and inflation port 400 in proximity to handle 111 and joined to inflation lumen 41 of shaft 115. Inflation port 400 and lumen 41 correspond with those embodiments shown in cross-section in FIGS. 4A–B. As shown in FIG. 5, lumen 43 passes from shaft into handle 111, terminating in a proximal opening, and wires 31 and 33, pass through lumens 51 and 53, from shaft 115 to slider 111A of handle 111. Arrow A illustrates motion of slider 111A to push or pull all wires 31–33 simultaneously and arrows E illustrate omni-directional motion of handle 111 in ball-and-socket joint 111B to manipulate wires 31–33 as previously discussed herein, in conjunction with FIGS. 3A–B.

FIG. 5B is a partial plan view of an alternate embodiment of a handle 311 for catheter 11 according to the present invention. Handle 311 includes multiple sliders 331, 332 and 333 (opposite 332, therefore not shown) joined to wires 31, 32 and 33, respectively of shaft 115. Sliders 331, 332 and 333 are moved individually to actuate omni-directional motion of manipulator 113 or to steer shaft 115.

Figure 6A:
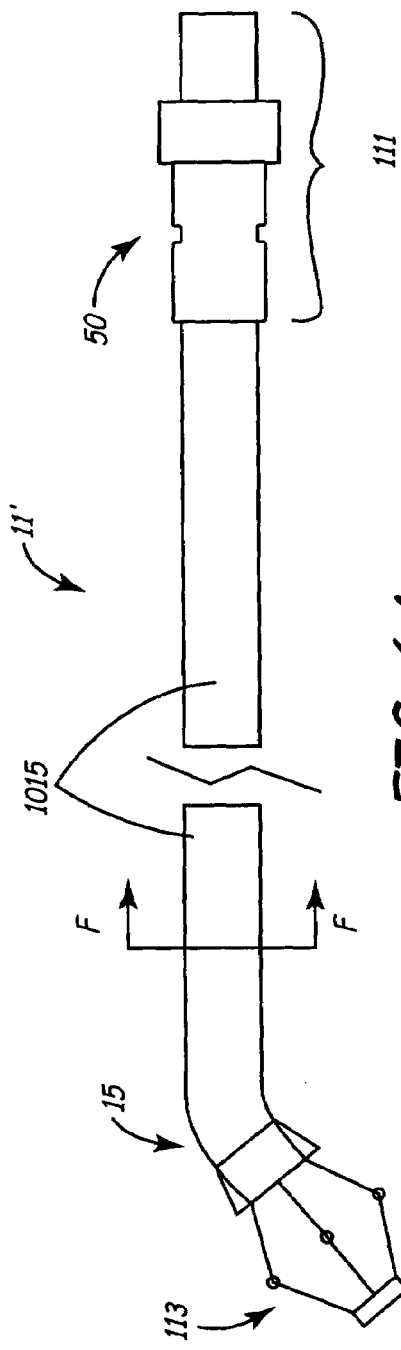
FIG. 6A is a plan view of an alternate embodiment of a delivery catheter.
Figure 6B:
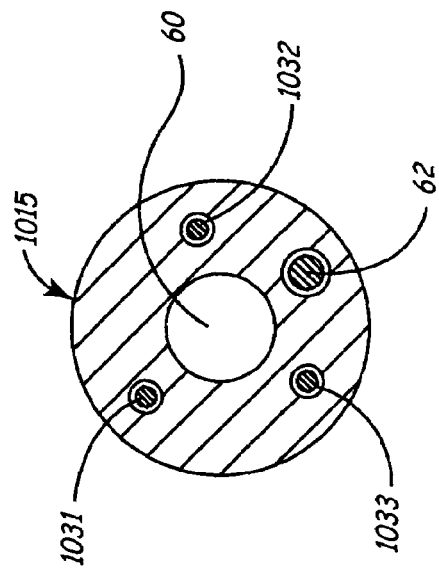
FIG. 6B is a section view of the shaft of FIG. 6A.

FIG. 6A is a plan view of an alternate embodiment of a delivery catheter 11'. As illustrated in FIG. 6A delivery catheter 11' includes a shaft 1015 wherein a distal end 15 is formed in a curve. According to an alternate embodiment, shaft 1015 is substituted for shaft 115 shown in FIG. 3A, therefore a general form and construction materials for shaft 1015 are similar to that described for shaft 115. FIG. 6B is a section view of shaft 1015 through section line F—F shown in FIG. 6A. FIG. 6B reveals a section of an elongated element 62 included in shaft 1015 to enable forming of distal end 15 as illustrated in FIG. 6A; also illustrated are control wires 1031, 1032, and 1033, adapted to actuate manipulator 113 via handle 111, and lumen 60 adapted to slideably engage a lead, such as lead 12, or a guide wire. In one embodiment, elongated element 62 extends from a proximal end 50 of shaft 1015 to distal end 15 in a form of a pull wire controlled by handle 111 to form distal end 15 of shaft 1015. In alternate embodiments, either extending only along a distal portion of shaft 1015 or extending along an entire length of shaft 1015, elongated element 62 is a malleable rod shapeable for setting a curve in a portion of shaft 1015.

Figure 7A:
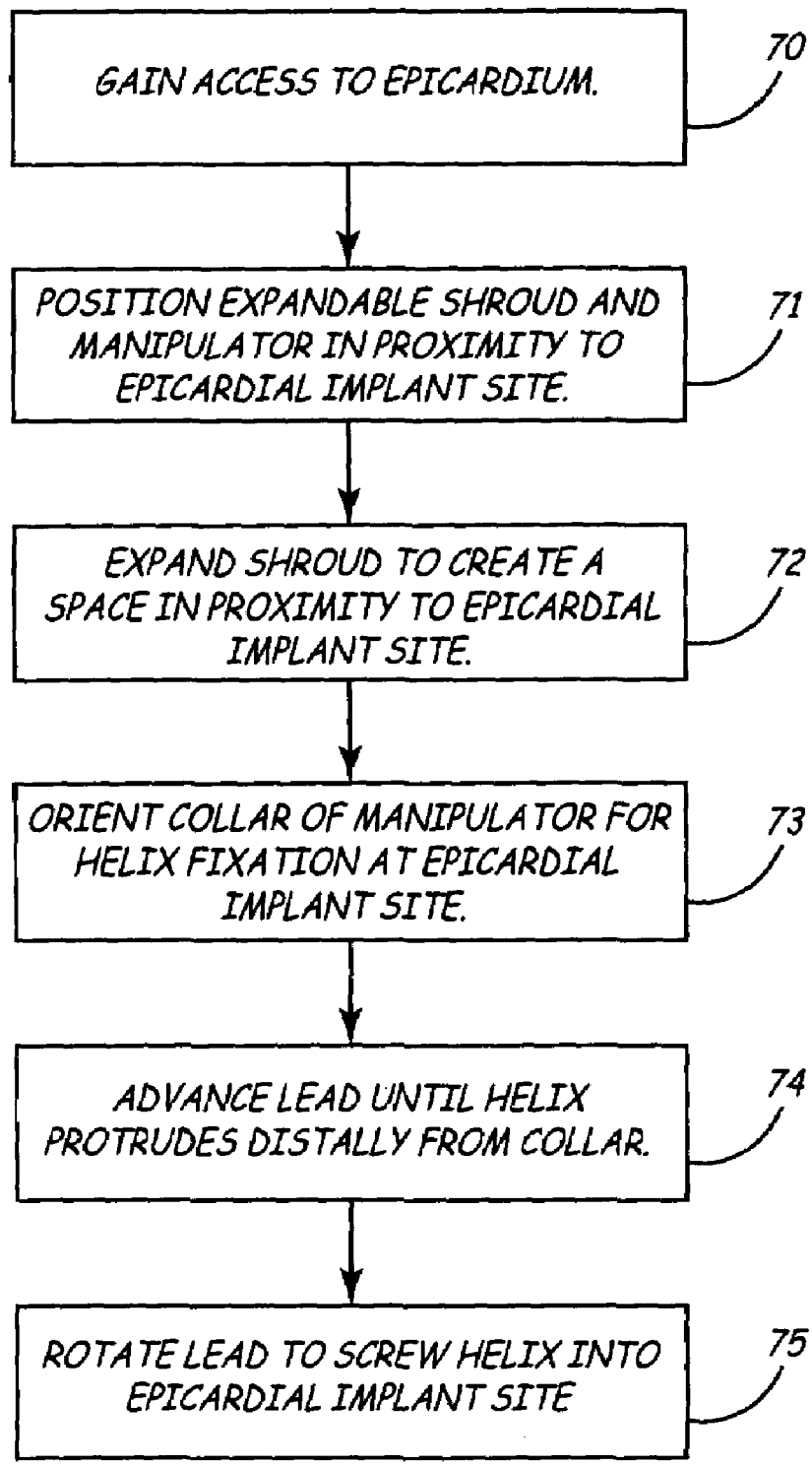
FIGS. 7A–B are flow charts illustrating steps included in alternate methods for implanting a lead using a delivery system according to the present invention.
Figure 7B:
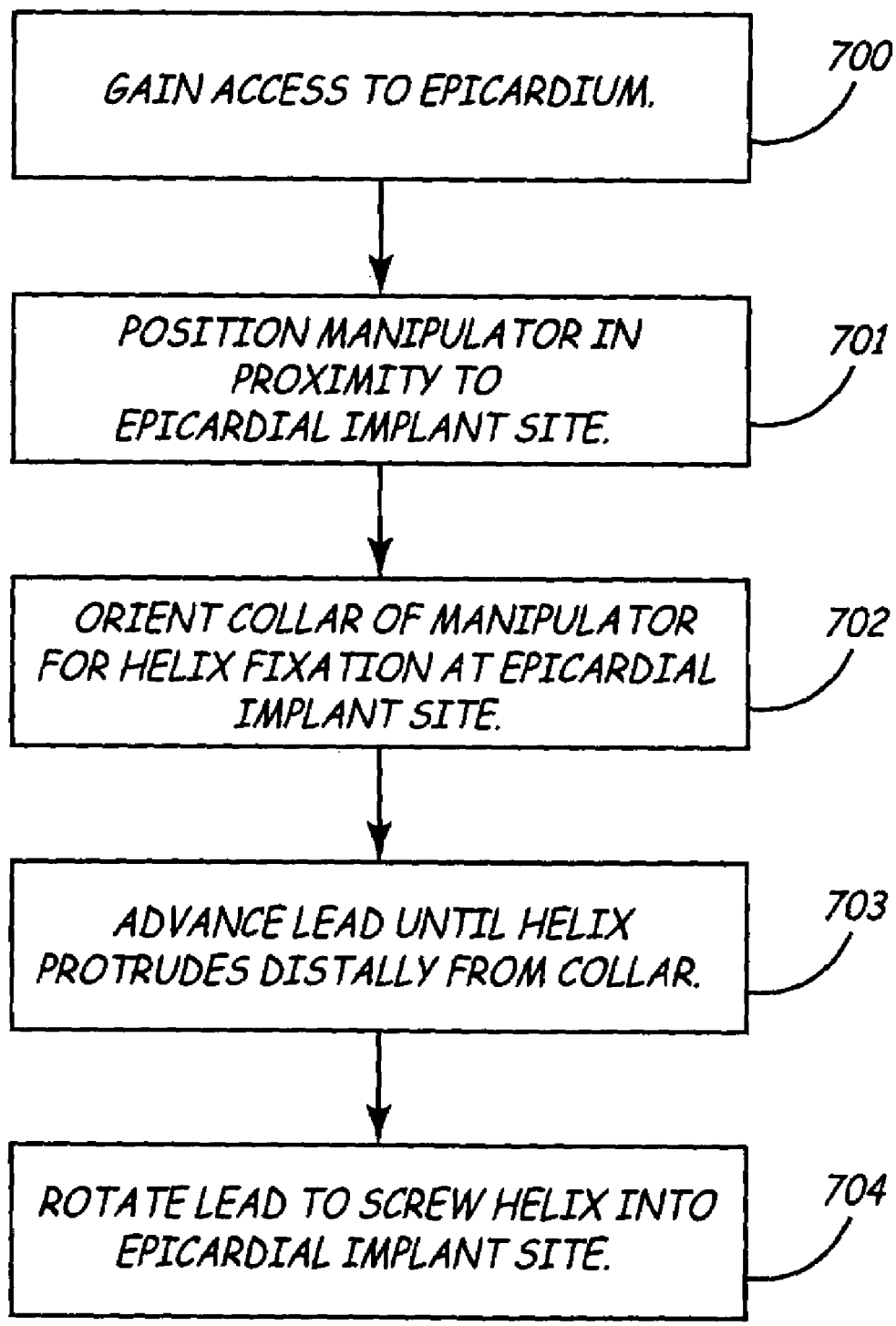

FIGS. 7A–B are flow charts illustrating steps included in alternate methods for implanting a lead using a delivery system according to the present invention. FIG. 7A shows steps associated with FIG. 1A, while FIG. 7B shows steps associated with FIG. 1B.

As described in conjunction with FIG. 1A, one way of gaining epicardial access (70) is via a sub-xyphoid approach wherein a guide wire is passed into a space between pericardial sac 2 and epicardial surface 1. Expandable shroud 114 and manipulator 113 are subsequently positioned in proximity to an epicardial implant site (71) either by being passed through sheath 10 or by being passed over the aforementioned guide wire. Shroud 114 is expanded to create a space at epicardial implant site (72), between epicardial surface 1 and pericardial sac 2, so that manipulator 113 has room to orient collar 1013 for helix fixation (73). Lead 12 is then advanced until helix 122 protrudes distally from collar 1013 (74). Alternately, steps 73 and 74 may be reversed such that lead 12 is positioned within delivery catheter 11 with helix 122 protruding distally from collar 1013 while manipulator 113 is orienting collar 1013. Once helix 122 is in contact with epicardial surface 1, lead 12 is rotated, at a proximal end, to screw helix 122 into epicardial surface 1 (704).

As described in conjunction with FIG. 1B, another way of gaining epicardial access (700) is via a mini-thoracotomy followed by excision of pericardial sac 2. Manipulator 113 is then positioned in proximity to an epicardial implant site (701) and steered to orient collar 1013 for helix fixation (702) without requiring shroud 114. Once collar 1013 is oriented, lead 12 is advanced until helix protrudes distally from collar 1013 (703) and then lead 12 is rotated to screw helix 122 into epicardial surface 1 (704).

An epicardial delivery system according the present invention, fulfilling the functions described herein is not limited to the embodiments described herein. For instance additional embodiments of a catheter, such as catheter 11, include additional elongated shaft lumens to facilitate fluid delivery for flushing or drug delivery at an implant site or to carry a fiber optic bundle to facilitate visualization during implant manipulation. These and other embodiments are within the scope of the following claims.

The invention claimed is:

1. A delivery system, comprising:
   a medical electrical lead having a fixation electrode at a distal end;
   an elongated delivery catheter having a shaft including a proximal end, a distal end, and a lumen extending from the proximal end to the distal end sized to accept insertion of said medical electrical lead; and
   an omni-directional movable wrist mechanism at the distal end of the catheter shaft and a handle at the proximal end of the catheter shaft, said movable wrist mechanism comprising a collar axially aligned with the catheter shaft lumen for passage of the fixation electrode through the collar, a plurality of manipulator arms attached to the collar, an actuator wire coupled to each of the arms and to the handle;

said handle being movable to control the actuator wires in creating an omni-directional motion of the movable wrist mechanism.

2. The delivery system of claim 1, wherein the plurality of manipulator arms includes three manipulator arms.

3. The delivery system of claim 1, wherein the medical electrical lead includes a tip and the collar includes a distal face; the tip of the medical electrical lead engaged against the distal face of the collar when the lead is engaged within the collar and within the lumen of the delivery catheter shaft.

4. The delivery system of claim 1, further comprising a shaft junction joining a proximal portion each of the plurality of arms to the shaft and wherein each of the plurality of arms includes a first flexible joint disposed between the shaft junction and the proximal portion of each of the plurality of arms, a second flexible joint disposed between the proximal portion and a distal portion of each of the plurality of arms, and a third flexible joint disposed between the distal portion of each of the plurality of arms and the collar.

5. The delivery system of claim 1, further comprising a pull wire adapted to form a curve in a distal portion of the shaft, the pull wire extending from the proximal end to a point in proximity to the distal end of the shaft.

6. The delivery system of claims 1, further comprising a malleable rod extending along a portion of the shaft.

7. The delivery system of claim 6, wherein the malleable rod extends along a distal portion of the shaft.

8. The delivery system of claim 6, wherein the malleable rod extends from a point in proximity to the proximal end of the shaft to a point in proximity to the distal end of the shaft.

9. The delivery system of claim 1, wherein the handle includes a ball-and-socket pivoting joint.

10. The delivery system of claim 1, wherein the handle includes a plurality of sliders joined to each of the plurality of control wires.

11. The delivery system of claim 1, further comprising:

an expandable shroud; and a second lumen extending from the proximal end to the distal end of the delivery catheter shaft and joined to the expandable shroud at the distal end of the shaft;

wherein the second lumen activates the shroud from the proximal end of the delivery catheter shaft.

12. The delivery system of claim 11, wherein the second lumen is formed within the shaft.

\* \* \* \* \*